United States Patent
Blomquist

(10) Patent No.: US 12,383,168 B2
(45) Date of Patent: *Aug. 12, 2025

(54) INSULIN PUMP BASED EXPERT SYSTEM

(71) Applicant: Tandem Diabetes Care, Inc., San Diego, CA (US)

(72) Inventor: Michael Blomquist, Blaine, MN (US)

(73) Assignee: Tandem Diabetes Care, Inc, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/624,350

(22) Filed: Apr. 2, 2024

(65) Prior Publication Data

US 2024/0245326 A1 Jul. 25, 2024

Related U.S. Application Data

(60) Continuation of application No. 17/715,735, filed on Apr. 7, 2022, now Pat. No. 11,986,292, which is a
(Continued)

(51) Int. Cl.
| | |
|---|---|
| *A61B 5/145* | (2006.01) |
| *A61B 5/00* | (2006.01) |
| *A61M 5/172* | (2006.01) |
| *G16H 10/20* | (2018.01) |
| *G16H 20/17* | (2018.01) |
| *G16H 40/63* | (2018.01) |
| *G16H 40/67* | (2018.01) |

(Continued)

(52) U.S. Cl.
CPC ........ *A61B 5/14532* (2013.01); *A61B 5/4839* (2013.01); *A61B 5/7475* (2013.01); *A61M 5/1723* (2013.01); *G16H 10/20* (2018.01); *G16H 20/17* (2018.01); *G16H 40/63* (2018.01); *G16H 40/67* (2018.01); *G16H 50/20* (2018.01); *A61B 5/7275* (2013.01); *A61B 2560/045* (2013.01); *A61M 2005/14208* (2013.01); *A61M 2205/3561* (2013.01); *A61M 2205/52* (2013.01); *A61M 2230/201* (2013.01)

(58) Field of Classification Search
CPC .............. A61M 5/1723; A61M 5/7275; A61M 5/4839; A61M 5/14532; A61M 2230/201; A61M 2205/18; G06F 19/3468; G06F 19/3456
See application file for complete search history.

(56) References Cited

U.S. PATENT DOCUMENTS

| 11,986,292 B2* | 5/2024 | Blomquist ........... A61B 5/4839 |
| 2005/0038332 A1* | 2/2005 | Saidara ................. G16H 40/67 128/920 |

* cited by examiner

*Primary Examiner* — Scott J Medway
*Assistant Examiner* — Anh Bui
(74) *Attorney, Agent, or Firm* — Merchant & Gould P.C.

(57) ABSTRACT

An apparatus comprising a pump configured to deliver insulin, an input configured to receive blood glucose data, a user interface, and a controller communicatively coupled to the pump, the input, and the user interface. The controller includes a blood glucose data module to compare the blood glucose data to a target blood glucose level for an insulin pump user. The controller is configured to present a question related to the blood glucose level via the user interface when the blood glucose level is different than the target blood glucose level, receive a response to the question via the user interface, and present a recommended user action based at least in part on the response. Other devices, systems, and methods are disclosed.

20 Claims, 4 Drawing Sheets

Related U.S. Application Data continuation of application No. 16/560,555, filed on Sep. 4, 2019, now Pat. No. 11,576,594, which is a continuation of application No. 15/830,415, filed on Dec. 4, 2017, now Pat. No. 11,298,053, which is a continuation-in-part of application No. 14/187,414, filed on Feb. 24, 2014, now Pat. No. 9,833,177, which is a continuation of application No. 13/465,570, filed on May 7, 2012, now Pat. No. 8,657,779, which is a division of application No. 11/755,480, filed on May 30, 2007, now Pat. No. 8,221,345.

(51) Int. Cl.
*G16H 50/20* (2018.01)
*A61M 5/142* (2006.01)

INSULIN PUMP BASED EXPERT SYSTEM

RELATED APPLICATIONS

This application is a continuation of U.S. application Ser. No. 17/715,735, filed Apr. 7, 2022, which is in turn a continuation of U.S. application Ser. No. 16/560,555 filed Sep. 4, 2019, now U.S. Pat. No. 11,576,595, which in turn is a continuation of U.S. application Ser. No. 15/830,415 filed Dec. 4, 2017, now U.S. Pat. No. 11,298,053 issued Apr. 12, 2022, which in turn is a continuation of U.S. application Ser. No. 14/187,414 filed Feb. 24, 2014, now U.S. Pat. No. 9,833,177 issued Dec. 5, 2017, which in turn application is a continuation of U.S. application Ser. No. 13/465,570 filed May 7, 2012, now U.S. Pat. No. 8,657,779 issued Feb. 25, 2014, which in turn is a division of U.S. application Ser. No. 11/755,480 filed May 30, 2007, now U.S. Pat. No. 8,221,345 issued Jul. 17, 2012, each of which is hereby fully incorporated herein by reference.

TECHNICAL FIELD

The field generally relates to patient insulin management devices and, in particular, but not by way of limitation, to systems, devices and methods for managing insulin therapy.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. Some insulin pumps can be difficult to program. Proper use of an insulin pump requires a user to go through a learning curve to properly treat their diabetes using the insulin pump.

SUMMARY

This document discusses, among other things, devices and methods for managing insulin therapy. A device example includes a pump configured to deliver insulin, an input configured to receive blood glucose data, a user interface, and a controller communicatively coupled to the pump, the input, and the user interface. The controller includes a blood glucose data module to compare the blood glucose data to a target blood glucose level for an insulin pump user. The controller is configured to present a question related to the blood glucose level via the user interface when the blood glucose level is different than the target blood glucose level, receive a response to the question via the user interface, and present a recommended user action based at least in part on the response.

A method example includes receiving blood glucose data into a device that includes an insulin pump, presenting a question related to a blood glucose level of an insulin pump user when determining, from the blood glucose data, that the blood glucose level is different from a target blood glucose level, receiving at least one response to the question into the insulin pump device, and presenting a recommended action for a user to take based, at least in part, on the response.

A system example includes a first device and a second device. The first device includes a pump configured to deliver insulin, an input that includes a communication port configured to receive blood glucose data, a user interface, and a controller communicatively coupled to the pump mechanism, the input, and the user interface. The controller includes a blood glucose data module configured to compare the blood glucose data to a target blood glucose level for an insulin pump user. The controller is configured for presenting a question related to the blood glucose level when the blood glucose level is different from a target blood glucose level, receiving a response to the question via the user interface, and presenting a recommended action for the user to take based at least in part on the response. The second device includes a user interface, a processor that includes a rule development module configured for developing the rule via the user interface, and a communication port configured to communicate the rule to the first device.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1A:
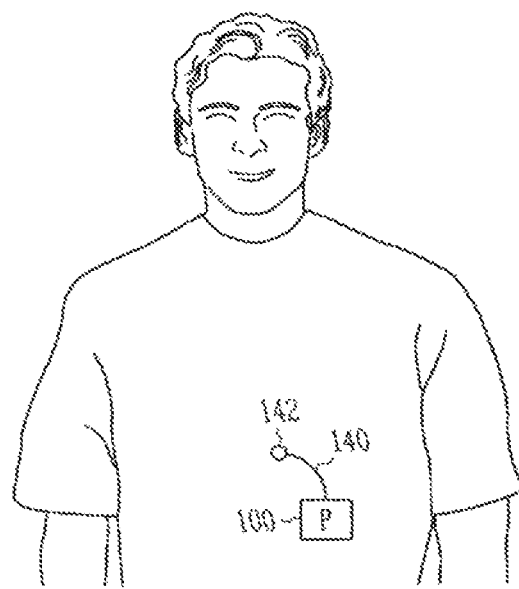
FIGS. 1A and 1B illustrate portions of a device that includes an insulin pump.
Figure 1B:
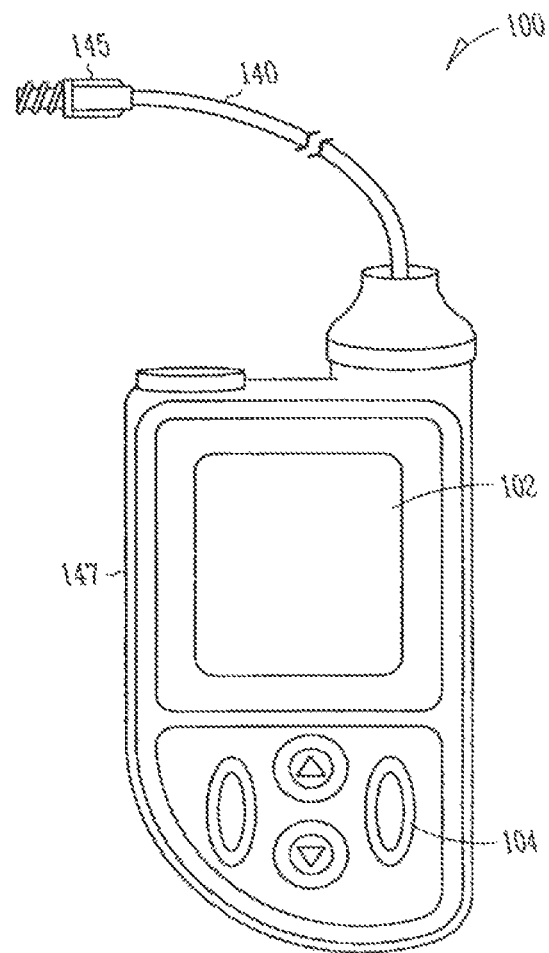

FIGS. 1A and 1B illustrate portions of a device 100 that includes an insulin pump. The device 100 includes a cassette or cartridge of insulin. The cartridge is connectable to infusion tubing 140 connectable to a patient such as by a Luer lock 145 or infusion set 142. The device 100 includes a display 102 and a user interface that may include the display 102 and include one or more keys 104. Because proper use of an insulin pump requires a user to go through a learning curve to properly treat their diabetes using the pump, it is desirable for a pump to provide assistance to the user, whether the user is a diabetic patient, a caregiver, or a clinician. Providing an expert system in an insulin pump device will provide assistance to the user to effectively treat their diabetes using the insulin pump device.

Figure 2:
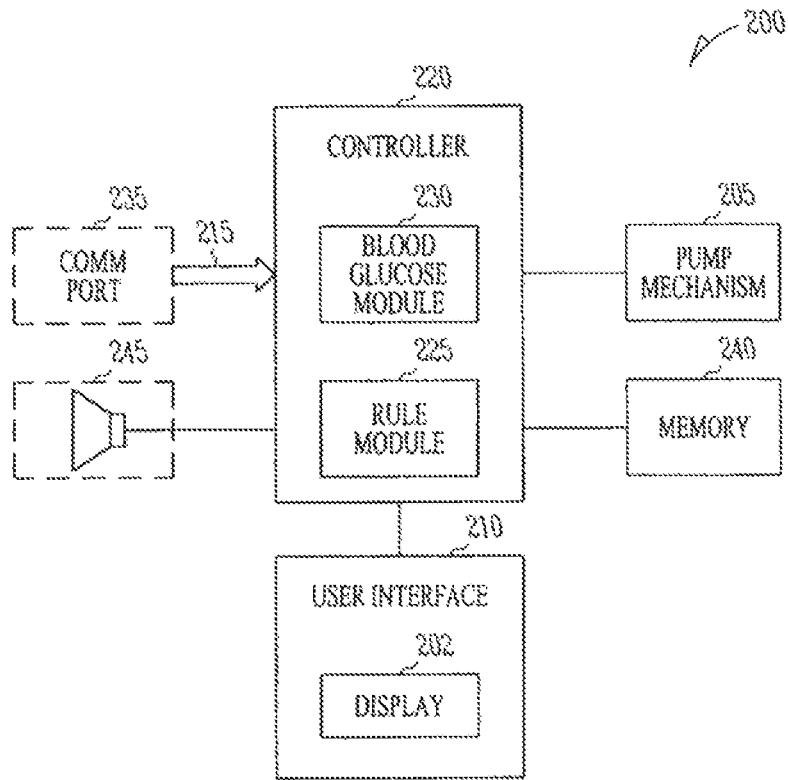
FIG. 2 is a block diagram of an example of portions of an insulin pump device.

FIG. 2 is a block diagram of an example of portions of an insulin pump device 200. The insulin pump device 200 includes a pump 205 or pump mechanism to deliver insulin to a subject, such as a positive displacement pump for example. The insulin pump device 200 also includes a user interface 210, an input 215, and a controller 220. The user interface 210 receives manual input from a user and may include one or more pushbuttons or a keypad. The user interface 210 may include a display 202 to provide instructions to the user. The user of the device may be a clinician or a diabetic patient. The display 202 may include a touchscreen.

The input 215 is configured to receive blood glucose data of a patient or subject. The input 215 may be coupled to a blood glucose monitor (GM) included in the insulin pump device 200 or the input 215 may include a communication port to receive the blood glucose data from a second separate device. In some embodiments, the communication port 235 is a wireless communication port configured to receive the blood glucose data from the separate device wirelessly. If the GM is a continuous GM, the continuous GM automatically collects the sampled blood glucose data in real time. The insulin pump device 200 may receive the blood glucose in real time as it is obtained or communicated at a later time. If the data is communicated at a later time, a timestamp may be included with the blood glucose data to indicate at what time the data was collected. In some embodiments, the input 215 is coupled to the user interface 210, and the user may manually input the data into the insulin pump device 200 through a keypad included in the user interface 210.

In some examples, the GM may require a prompt from the user to begin a blood glucose data measurement to obtain the blood glucose data. For example, the GM may require diabetes test strips to take a blood glucose measurement. The controller 220 recurrently presents a prompt to the user to begin a blood glucose measurement using the GM and obtain blood glucose data. In certain examples, the prompt is presented periodically. The prompt may be presented via the display 202. The prompt may be presented by activating a light emitting diode (LED) included in the insulin pump device 200. In some examples, the prompt is presented by audibly such as by a transducer or by a speaker instructing the user. The user then provides a new test strip to the GM when prompted during the correction factor test. In another example, the GM may include a drum of diabetes test strips and the user advances the drum to a fresh or unused test strip when prompted by the controller 220.

If the insulin pump device 200 includes a continuous GM, the input 215 may be coupled to blood glucose sensor circuit. The blood glucose sensor circuit includes a blood glucose sensor to produce a blood glucose signal representative of a blood glucose level of the patient. The blood glucose sensor may sense blood glucose concentration from blood or interstitial fluid. The blood glucose sensor circuit may include a sensor interface circuit to sample the blood glucose signal and may provide additional signal processing such as filtering or amplification for example. The blood glucose sensor circuit may provide sampled blood glucose data to the input 215. A description of a blood glucose sensor circuit can be found in Steil et al., U.S. Pat. No. 6,558,351, filed Jun. 1, 2000.

The controller 220 is operatively coupled to the pump mechanism 205, the input 215, and the user interface 210. The controller 220 can be implemented using hardware circuits, firmware, software or any combination of hardware, firmware and software. Examples, include a microcontroller, a logical state machine, and a processor such as a microprocessor, application specific integrated circuit (ASIC), or other type of processor. The controller 220 is configured to perform or execute a function or functions. Such functions correspond to modules, which are software, hardware, firmware or any combination thereof. Multiple functions are performed in one or more modules.

The controller 220 monitors the blood glucose data of the subject. The controller 220 includes a blood glucose data module 230. The blood glucose data module 230 uses the blood glucose data to determine whether a blood glucose level of the subject is different from a target blood glucose level. The target blood glucose level may include a specified range of blood glucose levels and the blood glucose data module 230 may determine whether the blood glucose data indicates the blood glucose of the pump user is outside of a specified range of blood glucose levels. Being outside of a range may include having a blood glucose level that is too high or too low. The blood glucose data module 230 may determine whether a blood glucose level is above an acceptable range of higher blood glucose level, or below an acceptable range of low blood glucose levels. The target or range may be stored in memory and be a programmable parameter available to the blood glucose data module 230. A clinician would specify the range of blood glucose levels for the patient. The range would depend on various factors for the patient such as weight, age, and level of activity of the patient for example.

If the blood glucose data module 230 determines that the blood glucose level of the subject is different from the target or the specified range of blood glucose levels, the controller 220 presents one or more questions related to the blood glucose level via the user interface 210. Preferably, the question is presented using the display 202. However, in some examples, the question may be presented audibly. Presenting the question audibly may be useful if the insulin pump user has difficulty seeing the display 202. The questions are designed to help a user to properly treat their diabetes using the insulin pump device 200 and even by programming the insulin pump device 200. In some examples, the controller 220 presents different questions according to different blood glucose levels. For example, the controller 220 may present different questions according to whether the blood glucose level of the patient is above 200 mg/dl, or above 300 mg/dl, or above 400 mg/dl. The clinician may program the different levels into the insulin pump device 200.

The user responds to the question through the user interface 210. Based at least in part on one or more responses, the controller 220 displays at least one recommended action for the user to take. As is discussed below, the recommended action may involve various user actions such as troubleshooting the insulin pump device 200, delivering insulin using the insulin pump device 200, initiating a measurement or test using the insulin pump device 200, or making lifestyle changes for example. In some examples, the recommended action for display may include contacting a physician. In some examples, the recommended action may be different according to the blood glucose level of the patient. For example, the controller 220 may present different actions according to whether the blood glucose level of the patient is above 200 mg/dl, or above 300 mg/dl, or above 400 mg/dl.

If the question is presented using a display 202, the device may include an alarm circuit 245 coupled to the controller 220 to draw the attention of the user to the display 202. The alarm circuit 245 may include an audible alarm, a visual indication such as a flashing light or flashing icon on the display, or the alarm circuit may mechanically vibrate the insulin pump device to draw attention of the user. The controller 220 activates the alarm circuit 245 if it is determined that the blood glucose level of the subject is outside of the specified range of blood glucose levels.

Figure 3:
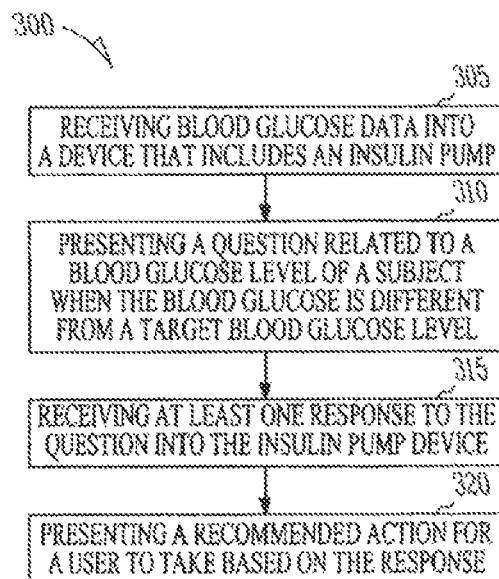
FIG. 3 shows an example of a method for managing insulin therapy.

FIG. 3 shows an example of a method 300 for managing insulin therapy. At block 305, blood glucose data is received into an insulin pump device 200. At block 310, at least one question related to a blood glucose level of a patient is presented when determining, from the blood glucose data, that the blood glucose level is outside of a range of blood glucose levels. The question may be presented on a display 202 included with the insulin pump device 200, or the question may be transmitted to a second device for display, such as a computer for example. This may be useful if a display 202 on the insulin pump device 200 is difficult for the user to read. In some examples, the second device presents the question audibly. The insulin pump and the second device may communicate wirelessly such as by radio frequency (RF) or infrared red (IR) communication. At block 315, at least one response to the question is received into the insulin pump device 200. The response may be received through a user interface. At block 320, at least one recommended action is presented for a user to take based, at least in part, on the response. The action may be presented audibly or visually, such as by a display for example.

Figure 4:
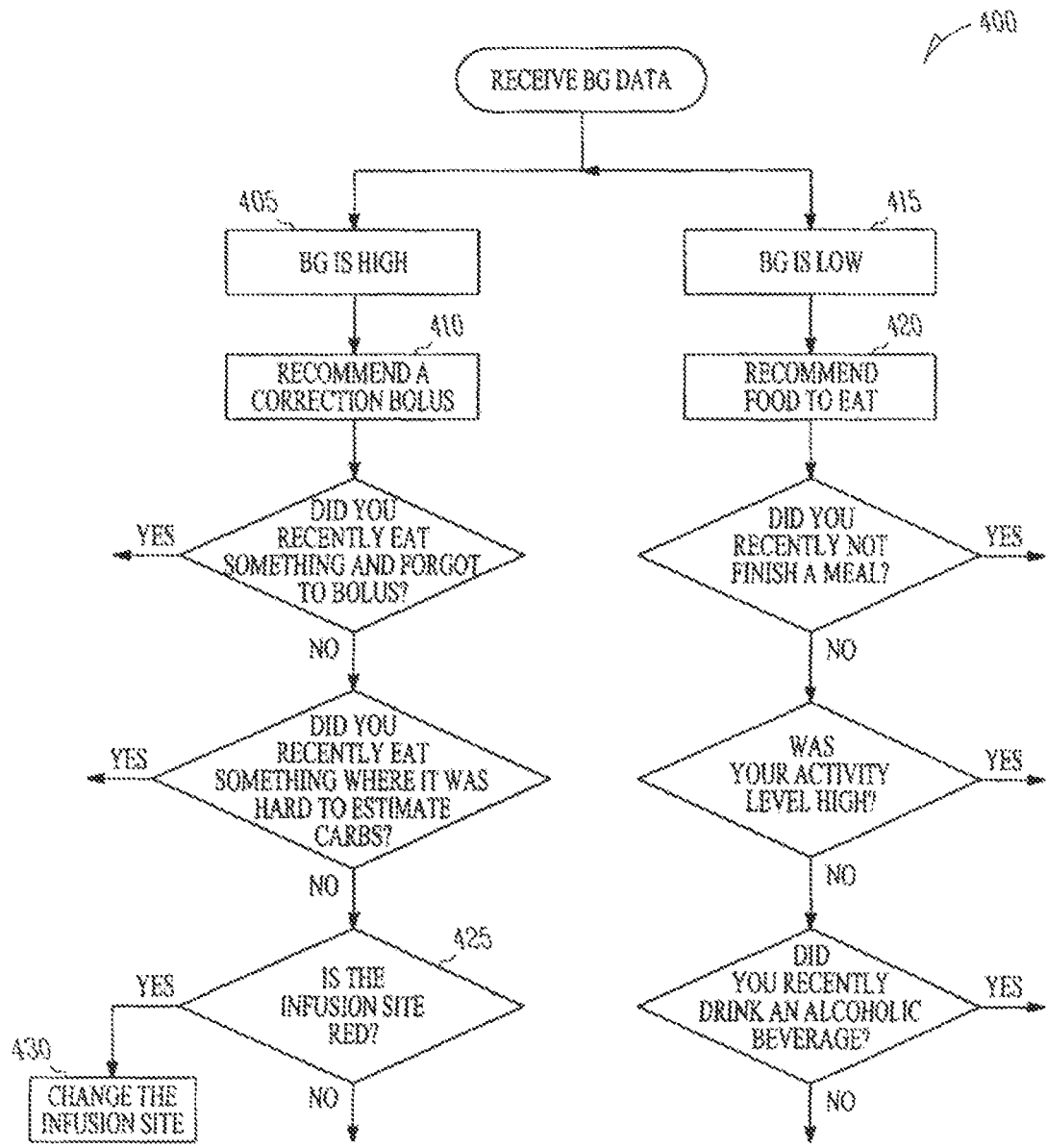
FIG. 4 shows a portion of an example of a decision tree to determine one or more questions for the user of an insulin pump device.

Returning to FIG. 2, in some embodiments, the controller 220 includes a rule module 225 to apply at least one rule to the blood glucose data to determine the question to be presented. In some embodiments, the rule includes a decision tree. FIG. 4 shows a portion of an example of a decision tree 400 to determine one or more questions for the user of the insulin pump device 200. In certain examples, the decision tree 400 may implemented with a series of IF-Then logic statements. The controller 220 traverses the decision tree 400 using various information such as the blood glucose data, responses from the user, or other data. If the blood glucose is high, the left portion of the decision tree 400 is traversed at block 405. The controller 220 may display a recommended action, such as the user taking a correction bolus at block 410, before asking one or more questions. If the blood glucose is low, the right portion of the decision tree 400 is traversed at block 415. The controller 220 may display a recommended action, such as the user eating food at block 420 before asking one or more questions. The controller 220 may display a picture or icon of food when making the recommendation.

In some examples, the rule module 225 applies the rule to the blood glucose data and to at least one user response to the question to determine the recommended action for display. For example, using the decision tree 400, if the blood glucose level is high, the controller 220 may display a question asking if the infusion site is red at block 425. If the user interface 210 receives a response from the user that the site is red, the controller 220 may display a recommendation that the user change the infusion site at block 430.

In some embodiments, the rule module 225 may include a look-up table stored in a memory. For example, if the blood glucose is low, the look up table may include a question as to whether the patient had a high activity level. If the user interface 210 receives a response that the activity level was high, the look up table includes a recommended action corresponding to a table entry for low blood glucose and high activity. The table entry may include a recommended action that the patient eat before the activity or lower a programmable basal rate of insulin before or during the activity. The table may include multiple dimensions to take into account multiple factors, responses, or other data. In some examples, the rule module 225 assigns weights to corresponding table entries. For example, receiving a response that the infusion set has visible blood may by weighted as a stronger indication to change the infusion site than if a response is received that the infusion site is red. In some examples, the rule module 225 uses one or more fuzzy logic rules to determine the question for display and any recommended action. The fuzzy logic rules may be used to blend any weighted questions, responses, or actions. In some examples, the rule module 225 uses a rule involving application of artificial intelligence methods to determine the questions and the actions to be presented.

In some examples, the rule module 225 may apply the rule to the blood glucose data and present a recommendation that the user initiate at least one blood glucose measurement. The measurement may be made using a second separate device that includes a GM, or the action may recommend making the measurement with the insulin pump device 200 if the device includes a GM.

Note that application of the rule by the rule module 225 may result in a series of questions displayed, responses by the user, and recommend actions. For example, the insulin pump device 200 may receive an indication that a recommended action was taken. The rule module 225 may apply the rule to the blood glucose data, the response to the question, and the indication that the action was taken to determine at least one of a further question and a further recommended action to be presented.

In some examples, the rule module 225 may apply the rule to the blood glucose data and present a recommendation that the user initiate a basal rate test. Basal rate refers to a type of twenty-four hour background infusion of insulin by an insulin pump that mimics the continuous background release of insulin from a normal pancreas. It is the rate of insulin delivery the patient normally needs independent of the consumption of meals. If the basal rate is inappropriate, blood glucose concentration levels may result that are out of a recommended or desired range. An insulin pump user may go through several iterations of trial and error before finding appropriate basal rates. Because a patient's basal insulin needs may change over time, such as with weight change or with a change in fitness level, basal rate testing may be performed periodically to ensure that an appropriate basal rate is being delivered by an insulin pump. Based on the blood glucose level, the rule module 225 determines that a recommendation to run a basal rate test (by either the insulin pump device 200 or a separate device) should be presented (such as by display). As a result of the basal rate test, the controller may display a recommendation to change a programmable basal rate pattern or profile of the insulin pump device 200. Descriptions of devices and methods that perform a basal rate test are found in Blomquist et al., "Basal Rate Testing Using Frequent Blood Glucose Input," U.S. patent application Ser. No. 11/685,617, filed Mar. 13, 2007, which is incorporated herein by reference.

In some examples, the rule module 225 may apply the rule to the blood glucose data and present a recommendation that the user initiate a carbohydrate ratio test if the blood glucose level is outside a desired range. A carbohydrate ratio refers to the amount of carbohydrates covered by a unit of insulin. It is sometimes referred to as a carbohydrate factor, or carb factor, and is typically specified as grams of carbohydrates per unit of insulin. The insulin pump device 200 may use the carbohydrate ratio to automatically determine a carbohydrate insulin bolus amount required to match a number of carbohydrates ingested by the patient, or at least to keep post-meal blood glucose within a range that is healthy for a patient. For example, the patient may plan to eat seventy grams of carbohydrates. If the carbohydrate ratio is ten grams of carbohydrates per unit of insulin, the insulin pump device 200 would determine that seven units of insulin are required to cover the carbohydrates.

The appropriate carbohydrate ratio may vary from person to person, yet it is important for an insulin pump to use an appropriate carbohydrate ratio. If a carbohydrate ratio is too small, the pump may determine a carbohydrate bolus that is too large for the carbohydrates consumed. This may cause a low blood glucose level within a few hours of the carbohydrate bolus (e.g., the blood glucose level drops below 70 mg/dl). If a carbohydrate bolus is too large, the insulin pump device 200 may determine a carbohydrate bolus that is too small for the carbohydrates consumed. This may cause a high blood glucose level within a few hours of a carbohydrate bolus. Based on the blood glucose level, the rule module 225 determines that a recommendation to run a carbohydrate ratio test should be presented. As a result of the carbohydrate ratio test, the controller 220 may present a recommendation to change a carbohydrate insulin bolus pattern or profile delivered by the insulin pump device 200. For example, the controller 220 may recommend a carbohydrate bolus pattern that includes an extended carbohydrate bolus or a combination bolus. Descriptions of devices and methods that perform a carbohydrate ratio test are found in Blomquist, "Carbohydrate Ratio Testing Using Frequent Blood Glucose Input," U.S. patent application Ser. No. 11/679,712, filed Feb. 27, 2007, which is incorporated herein by reference.

In some examples, the rule module 225 may apply the rule to the blood glucose data and present a recommendation that the user initiate a correction factor test. A correction factor refers to the amount in drop in blood sugar, or blood glucose, for one unit of insulin. It is measured in milligrams per deciliter (mg/dl) per unit in the U.S. and in millimoles (mmol) per unit in other countries. The insulin pump device 200 may use the correction factor to automatically determine a bolus amount required for a high reading or a reduction in a meal bolus for a below-target reading. The insulin pump device 200 may also use the correction factor to calculate the amount of carbohydrates a patient should eat to bring low blood sugar up to a target blood sugar level. An appropriate correction factor brings a high blood glucose reading down using an automatically determined correction bolus without a risk of going low.

The appropriate correction factor varies from person to person. It is important for an insulin pump to use an effective correction factor. If a correction factor for a pump is set too high, the blood glucose may not actually be dropping as much as estimated and could lead to high blood glucose levels. If the correction factor is set too low, a correction bolus may provide too much insulin and result in a low blood glucose level. As a result of the carbohydrate ratio test, the controller 220 may display a recommendation to change an insulin correction bolus pattern or profile, such as to include an extended bolus or a combination bolus for example. Descriptions of devices and methods that perform a carbohydrate ratio test are found in Blomquist et al., "Correction Factor Testing Using Frequent Blood Glucose Input," U.S. patent application Ser. No. 11/626,653, filed Jan. 24, 2007, which is incorporated herein by reference.

In some embodiments, the rule module 225 may receive an updated or new rule or a modification to the rule. In certain embodiments, the insulin pump device 200 includes a communication port 235 coupled to the input 215. The communication port 235 receives the rule into the insulin pump device 200 from a second separate device. In some examples, the communication port 235 is a wireless port and receives the rule wirelessly. The second device may be a computer or a personal data assistant (PDA). The second device may provide an environment (e.g., such as through software) for a diabetes professional, clinician, or other caregiver to customize the rule. In some examples, the environment allows the clinician to customize a decision tree or look up table.

Figure 5:
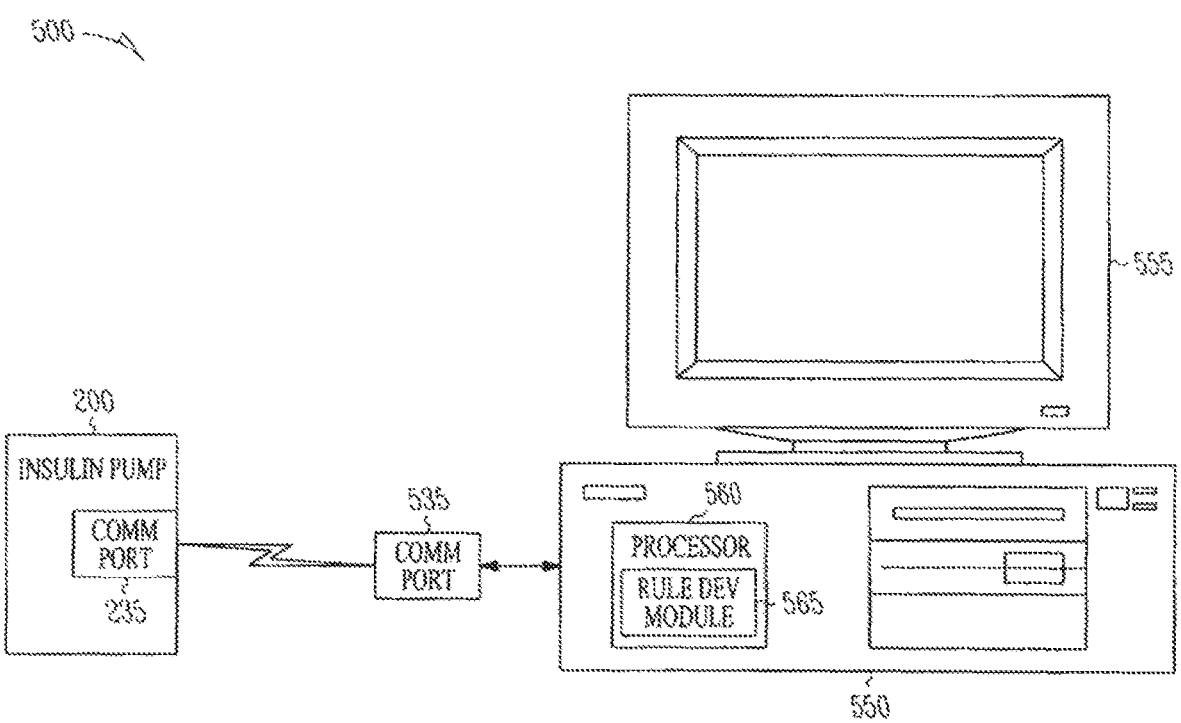
FIG. 5 shows an example of a portion of a system that provides an environment to customize a rule for an insulin pump device.

FIG. 5 shows an embodiment of a portion of a system 500 that provides an environment to customize rules in the rule module 225. The system 500 includes an insulin pump device 200 and a computing device 550. The insulin pump device 200 includes a communication port 235 to communicate information with the computing device 550. The communication port 235 shown is a wireless port that communicates wirelessly with the computing device 550, such as a radio frequency (RF) port or infrared (IR) port for example. The communication port 235 may receive blood glucose data from a third device, such as a GM for example. In certain examples, the insulin pump device 200 receives the blood glucose data from a GM when the GM is communicatively coupled to the communication port 235. The insulin pump device 200 is able to communicate information with the computing device 550 when the GM is not communicatively coupled to the insulin pump device 200. In some examples, the communication port 235 may be a wired port, such as a serial port for example, to communicate with the computing device 550.

The computing device 550 may be a personal computer (PC), laptop computer, or a personal data assistant (PDA). The computing device 550 includes a user interface 555 that includes a display and may include at least one of a keyboard or keypad and a computer mouse. The computing device 550 also includes a processor 560 communicatively coupled to the user interface 555. The processor 560 can be a microprocessor, application specific integrated circuit (ASIC), or other type of processor.

The processor 560 includes a rule development module 565 that provides doctors or clinical experts the ability to develop and generate a new rule or rule set or modify rules via the user interface 555. The computing device 550 includes software that provides a flexible framework to create or modify rules such as by updating a graphical decision tree, a multidimensional table, or other type of logical rule. The software may be included in a computer readable medium, such as a compact disc (CD) for example, or the software may be downloaded to the computing device 550 from remote storage, such as from a server for example. The rule development module 565 develops a rule to be applied to the blood glucose data received into the insulin pump device 200, and may develop a rule that is also applied to at least one of physiologic data, demographic data, patient lifestyle data, insulin delivery history data, and blood glucose history data to generate a recommended action. The computing device 550 includes a communication port 535 to communicate information with the insulin pump device 200. The computing device 550 uses the communication port 535 to communicate the rule to the insulin pump device 200.

Once a rule is developed, the doctor or clinical expert could publish or otherwise share a rule or set of rules. In some embodiments, rule sets can be stored in remote storage, such as a server for example. The computing device 550 may be connected to a communication network, such as the internet or a cell phone network for example. A doctor or clinical expert may download a rule or rule set from the remote storage and either download the rule set directly from the computing device 550 into the insulin pump device 200 or modify the rule or rule set before downloading the modified rule or rule set to the insulin pump device 200.

Returning to FIG. 2, in some embodiments, the user interface 210 and the input 215 receive modifications to the rule that are entered into the insulin pump device 200 manually by the user via the user interface 210. For example, the user may step through the rule with the aid of the display 202. The user may then alter the rule with a keypad included in the user interface 210. For example, the user may enter a new look up table entry using the key pad, or add another branch to a decision tree or edit a branch of the decision tree. In certain embodiments, an entire new rule or rule set is entered manually into the insulin pump device 200 via the user interface 210.

In some embodiments, the insulin pump device 200 stores data to track effectiveness of a new rule or modified rule. For example, the insulin pump device 200 may track the number of times the blood glucose level of the patient returned to the target blood glucose level or to within the target range of levels after application of the rule. The effectiveness may be displayed as a percentage or as X successes out of Y applications on either a display 202 of the insulin pump or uploaded and displayed on a separate device, such as the computing device 550 in FIG. 5 for example.

If a rule or rule set is downloaded into multiple devices, the effectiveness of the rule set for multiple device may be tracked. The stored data related to the effectiveness may be uploaded to a remote server and the server tracks the overall effectiveness of the rule over the multiple devices. The overall effectiveness may be useful to a clinician in determining whether to download a particular rule or rule set to the insulin pump device 200.

In some embodiments, controller 220 determines a rate of change of a blood glucose level of the subject from the blood glucose data. For example, the controller 220 may determine that the blood glucose concentration level is increasing or decreasing at a rate of 2 to 4 mg/dl/min (milligrams per deciliter per minute). The rule module 225 may apply one or more rules to the rate of change of a blood glucose level to determine at least one of a question for display or one or more recommended actions for display. For example, the blood glucose level of the user may not be high, but the rate of change of blood glucose may be increasing at such a rate to indicate there is a risk of the blood glucose level going high. Conversely, the blood glucose level of the user may not be below a blood glucose target, but the rate of change of blood glucose may be decreasing at such a rate to indicate there is a risk of the blood glucose level going low.

In some examples, the rule module 225 may apply the rules to at least one of the blood glucose data, the rate of change of blood glucose data, and a response to a question to determine a subsequent question or recommended action for display by the controller 220. For example, if the blood glucose level is high and increasing at a certain rate, the rule module 225 may apply the rule to determine that a recommended action to take a correction bolus should be presented before presenting a question. In another example, if the blood glucose level is high and decreasing at a certain rate, the rule module 225 may apply the rule to determine that a recommended action to take a correction bolus should not be displayed and proceed to displaying a question such as whether the patient ate something where it was difficult to estimate the carbohydrates.

According to some embodiments, the controller 220 may display a recommendation that the patient consume carbohydrates if the blood glucose level is low or there is a risk of blood glucose level going low. In some examples, the memory 240 may store a database of food options in association with a known amount of carbohydrates. The recommended action presented by the controller 220 may include displaying a food option for consumption that is included in the database.

In some embodiments, the controller 220 determines an amount of carbohydrates for the patient to consume and presents a food option accordingly. For example, assume that the blood glucose level of a patient is 40 mg/dl below a desired range of blood glucose levels. The correction factor is stored in the insulin pump device 200 and is 1 unit per 80 mg/dl. The controller 220 determines that −0.5 unit of insulin (−40/80) is required to bring the blood glucose level back to the target level or range. Further assume that the carbohydrate ratio of the patient is 20 grams of carbohydrates per unit of insulin (20 g/u). The controller 220 multiplies the amount of insulin by the carbohydrate ratio to determine that the patient should eat 10 grams of carbohydrates [(0.5)(20)]. The insulin calculation module 125 may take into account additional factors such as the health status of the patient and the activity level of the patient in recommending the carbohydrate amount. In some example, the food option may be displayed using an icon or picture of food.

According to some embodiments, the input 215 receives physiologic data into the insulin pump device 200 from a separate second device. The data may be received through the input 215 or another input. In some embodiments, the insulin pump device 200 receives the physiologic data through a communication port 235. In some examples, the insulin pump device 200 receives the physiologic data through the same communication port 235 that receives the blood glucose data. In some examples, the second device includes a temperature monitor and the physiologic data includes a patient temperature. In some examples, the second device includes an activity monitor and the physiologic data includes an indication of a level of patient activity.

The rule module 225 may apply one or more rules to the physiologic data to determine a question for display. The rule module 225 may apply one or more rules to the physiologic data and a response to the question to determine one or more recommended actions for display. In some examples, the rule module 225 may apply one or more rules to the physiologic data, the blood glucose data, at least one question response to determine a question or recommended action for display. The controller 220 displays the questions and recommended actions.

In some embodiments, the insulin pump device 200 includes a memory 240 communicatively coupled to the controller 220. The memory 240 may store demographic data of the subject. The demographic data includes such information as a patient's weight, age, and gender for example. The demographic data may be received from a second device or through the user interface 210. The rule module 225 may apply one or more rules to the demographic data to determine a question to be presented. The rule module 225 may apply one or more rules to the demographic data and a response to the question to determine and/or adjust one or more recommended actions. In some examples, the rule module 225 may apply one or more rules to the demographic data, the blood glucose data, at least one question response to determine a question or recommended action for display.

In some embodiments, the controller 220 adjusts the questions and recommended actions based on the demographic data. For example, the controller 220 may use a different set of questions and recommended actions when the demographic data indicates that the patient is a child than when the demographic data indicates the patient is an adult.

In some embodiments, the memory 240 may store lifestyle data of the subject. The lifestyle data includes such information as whether a patient tends to eat high glycemic index foods, drinks alcohol, smokes, eats a bedtime snack, a health status of the patient, whether the patient is typically under stress, whether the patient tends to be active, and the amount time the patient spends exercising, for example. The lifestyle data may be received from a second device or entered through the user interface 210. The rule module 225 may apply one or more rules to the lifestyle data to determine a question for display. The rule module 225 may apply one or more rules to the lifestyle data and a response to the question to determine one or more recommended actions for display. In some examples, the rule module 225 may apply one or more rules to the lifestyle data, the blood glucose data, at least one question response to determine a question or recommended action for display.

A recommended action may include a change to at least one aspect of the patient's lifestyle, such as to skip the bedtime snack or to eat lower glycemic index meals, for example. In some examples, the recommended action may include recommending patient training. In certain examples, the insulin pump device 200 may present a recommendation that the patient be trained in carbohydrate counting. In certain examples, the insulin pump device 200 may recommend that the patient be trained in managing their exercise. In certain examples, the insulin pump device 200 may recommend that the patient be trained in using the insulin pump when the patient is sick. In certain examples, the insulin pump device 200 may recommend that the patient be trained in proper infusion site care.

In some embodiments, the memory 240 may store insulin delivery history data of the patient. Insulin delivery history data may include a time duration since the last meal bolus, how long since the cartridge was changed, and whether there have been any recent changes to programming parameters and what those changes were for example. The rule module 225 may apply one or more rules to the insulin delivery history data to determine a question to be presented. The rule module 225 may apply one or more rules to at least one of the insulin delivery history data, the blood glucose data, and a response to a question to determine one or more recommended actions.

In some embodiments, the memory 240 may store blood glucose history data of the subject. Blood glucose history data may include blood glucose data from a previous time period, such as two hours or 24 hours in the past for example. The data may be received from a GM included in the insulin pump device 200 or from a GM included in a separate device. In some examples, the blood glucose history data may be received from a separate computing device such as a PC, laptop, or PDA configured to communicate with the insulin pump device 200. The controller 220 may generate a prompt to download blood glucose history data from the second separate device, such as a prompt on a display 202, an LED prompt, or an audible prompt. The rule module 225 may apply one or more rules to the blood glucose history data to determine a question to be presented. The rule module 225 may apply one or more rules to at least one of the blood glucose history data, the blood glucose data collected in real time, and a response to a question to determine one or more recommended actions.

The patient may experience trouble with the insulin pump device 200 itself. According to some embodiments, the recommended action presented by the controller 220 includes actions for troubleshooting the insulin pump device 200. If the blood glucose level is low, the recommended actions may include checking or changing the insulin cartridge, the infusion set, the infusion set tubing, and/or the infusion site. For example, if the insulin pump device 200 stores the time since the cartridge was changed, the rule module 225 may determine that it is time for a new cartridge and display instructions to check whether the cartridge is low or change the cartridge. If it has been a short time since the cartridge was changed, the rule module 225 may eliminate the cartridge as the problem and display instructions to check or change the infusion set or the infusion site.

In another example, the user may respond that the cartridge was checked. The rule module 225 may apply the rule to the blood glucose level and the response and eliminate the cartridge as the problem. The insulin pump device 200 and the user may then step through response and actions that instruct the user to troubleshoot the infusion set and site. The controller 220 may also present a recommendation to change the type of insulin. For example, the rule module 225 may determine that the delay for uptake is too slow and recommend that the patient use a type of insulin with faster uptake. The controller 220 may also present a recommendation to change an insulin pump executable program and to see a diabetes professional. The controller may present a question whether the infusion set has visible blood and recommend that the infusion site be changed if there is visible blood. In some examples, the controller 220 may display a device error code and a recommendation to see the diabetes professional rather than present instructions to the user or patient that the pump program should be changed. The diabetes professional interprets the error code to determine the recommended action.

According to some examples, the blood glucose data module 230 may determine from the blood glucose data that a blood glucose level of the subject is at a target blood glucose level or within a specified range of blood glucose levels. The rule module 225 may determine one or more recommend actions for the patient to take that are related to maintaining normoglycemia. The rule module 225 may apply the rule to the blood glucose data and at least one of the physiologic data, the demographic data, the lifestyle data, the blood glucose history data, the insulin delivery history data, question responses, and previous actions taken to make the recommendation. The controller 220 displays the recommended action. For example, the controller 220 may ask lifestyle questions when blood glucose data is in the normoglycemic range. The controller 220 may aggregate insulin pump data and answers to the questions from various times when the blood glucose data values were in range and help the patient identify lifestyle or therapy patterns that promote good glycemic control.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

The invention claimed is:

1. A method, comprising:
   receiving sensor glucose data representative of a blood glucose level of a user;
   monitoring the sensor glucose data while a basal rate of insulin is being delivered to the user;
   comparing the sensor glucose data to a target low glucose level;
   determining a rate of change of the blood glucose level of the user from the sensor glucose data;
   generally continuously monitoring the rate of change;
   determining based on the monitoring of the rate of change that, although the sensor glucose data does not indicate that the glucose level of the user is below the target low glucose level that the rate of change indicates that the glucose level of the user is at risk of going below the target low glucose level due to the basal rate of insulin being delivered to the user;
   providing a notification indicating the risk of going below the target low glucose level.

2. The method of claim 1, wherein providing the notification indicating the risk of going below the target low glucose level includes providing a message relating to a corrective action responsive to the risk of going below the target low glucose level.

3. The method of claim 2, wherein the corrective action is a recommendation to ingest carbohydrates.

4. The method of claim 1, further comprising implementing a corrective action in response to the risk of going below the target low glucose level.

5. The method of claim 4, wherein the implemented corrective action is providing a recommendation to ingest carbohydrates.

6. The method of claim 1, wherein determining that, although the sensor glucose data does not indicate that the glucose level of the user is below the target low glucose level that the rate of change indicates that the glucose level of the user is at risk of going below the target low glucose level includes applying one or more rules to the rate of change.

7. The method of claim 1, further comprising presenting a recommendation to reduce the basal rate of insulin to the user.

8. A method, comprising:
   receiving sensor glucose data representative of a blood glucose level of a user;
   monitoring the sensor glucose data while a basal rate of insulin is being delivered to the user;
   comparing the sensor glucose data to a target low glucose level;
   determining a rate of change of the blood glucose level of the user from the sensor glucose data;
   generally continuously monitoring the rate of change;
   determining, based on the monitoring of the rate of change that, although the sensor glucose data does not indicate that the glucose level of the user is below the target low glucose level that the rate of change indicates that the glucose level of the user is at risk of going below the target low glucose level due to the basal rate of insulin being delivered to the user; and
   implementing a corrective action in response to the risk of going below the target low glucose level.

9. The method of claim 8, wherein the implemented corrective action is providing a recommendation to ingest carbohydrates.

10. The method of claim 8, further comprising providing a notification on a user interface relating to the risk of going below the target low glucose level.

11. The method of claim 10, wherein providing a notification relating to the risk of going below the target low glucose level includes providing a message relating to the corrective action.

12. The method of claim 11, wherein the corrective action is a recommendation to ingest carbohydrates.

13. The method of claim 12, wherein determining that, although the sensor glucose data does not indicate that the glucose level of the user is below the target low glucose level that the rate of change indicates that the glucose level of the user is at risk of going below the target low glucose level includes applying one or more rules to the rate of change.

14. The method of claim 8, further comprising presenting a recommendation to reduce the basal rate of insulin to the user.

15. A method, comprising:
receiving sensor glucose data representative of a blood glucose level of a user;
comparing the sensor glucose data to a target low glucose level;
determining a rate of change of the blood glucose level of the user from the sensor glucose data;
generally continuously monitoring the rate of change;
determining based on the monitoring of the rate of change that a future glucose level of the user is likely to be below the target low glucose level;
providing a notification indicating the future glucose level is likely to be below the target low glucose level.

16. The method of claim 15, wherein providing a notification that the future glucose level is likely to be below the target low glucose level includes providing a message relating to a corrective action.

17. The method of claim 16, wherein the corrective action is a recommendation to ingest carbohydrates.

18. The method of claim 15, further comprising implementing a corrective action in response to the future glucose level being likely to be below the target low glucose level.

19. The method of claim 18, wherein the implemented corrective action is providing a recommendation to ingest carbohydrates.

20. The method of claim 15, further comprising presenting a recommendation to reduce the basal rate of insulin to the user.

* * * * *